(12) United States Patent
Suzuki

(10) Patent No.: US 9,378,434 B2
(45) Date of Patent: Jun. 28, 2016

(54) IMAGE ANALYSIS METHOD AND IMAGE ANALYSIS DEVICE

(71) Applicant: OLYMPUS CORPORATION, Tokyo (JP)

(72) Inventor: Akemi Suzuki, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 289 days.

(21) Appl. No.: 13/870,638

(22) Filed: Apr. 25, 2013

(65) Prior Publication Data

US 2013/0236060 A1 Sep. 12, 2013

Related U.S. Application Data

(63) Continuation of application No. PCT/JP2010/069365, filed on Oct. 29, 2010.

(51) Int. Cl.
*G06K 9/62* (2006.01)
*G06K 9/00* (2006.01)
(Continued)

(52) U.S. Cl.
CPC ............ *G06K 9/628* (2013.01); *G01N 21/6408* (2013.01); *G01N 21/6458* (2013.01); *G06K 9/0014* (2013.01); *G06T 5/50* (2013.01); *G06T 7/0012* (2013.01); *G06T 2207/10056* (2013.01); *G06T 2207/10064* (2013.01); *G06T 2207/30024* (2013.01)

(58) Field of Classification Search
CPC .................... G06T 5/50; G06T 7/0012; G06T 2207/20216; G06T 2207/20224; G06T 2207/10064; G01N 21/6408; G01N 21/6458; G06K 9/00147; G01J 3/2889

USPC .......................... 382/128, 133, 224, 228, 236
See application file for complete search history.

(56) References Cited

U.S. PATENT DOCUMENTS

2009/0010551 A1* 1/2009 Matsuda ....................... 382/228
2009/0238435 A1* 9/2009 Shields ......................... 382/133
(Continued)

FOREIGN PATENT DOCUMENTS

JP 2004-108892 4/2004
JP 2004-354348 12/2004
(Continued)

OTHER PUBLICATIONS

Digman, et al. "Measuring Fast Dynamics in Solutions and Cells with a Laser Scanning Microscope." Biophysical Journal. 89. (2005): 1317-1327. Print.*

(Continued)

*Primary Examiner* — Michael A Newman
(74) *Attorney, Agent, or Firm* — Kenyon & Kenyon LLP

(57) ABSTRACT

An image analysis method includes acquiring fluorescent images of frames in time-series. Each fluorescent image comprises pixels in which pixel data are acquired in the time-series. The method further includes setting analysis areas to the acquired fluorescent images, calculating a classification value of the analysis areas, classifying the images into one or more groups on the basis of the classification value, calculating an average image of the analysis area every group, subtracting the average image from each image of the analysis area every group to calculate a new image of the analysis area, and calculating a correlation value on the basis of the new images every group.

18 Claims, 7 Drawing Sheets

(51) Int. Cl.
*G06T 7/00* (2006.01)
*G06T 5/00* (2006.01)
*G01N 21/64* (2006.01)
*G06T 5/50* (2006.01)

(56) References Cited

U.S. PATENT DOCUMENTS

2010/0272358 A1* 10/2010 Kanda .......................... 382/173
2011/0025880 A1* 2/2011 Nandy ....................... 348/226.1

FOREIGN PATENT DOCUMENTS

| JP | 2005-291762 | 10/2005 |
|---|---|---|
| JP | 2006-078377 | 3/2006 |
| JP | 2007-093277 | 4/2007 |
| JP | 2010-217104 | 9/2010 |
| JP | 2010-217761 | 9/2010 |
| JP | 2010-237116 | 10/2010 |
| JP | 2010-281735 | 12/2010 |
| WO | WO 20071037253 | 4/2007 |
| WO | WO 2008/087869 | 7/2008 |

OTHER PUBLICATIONS

Digman, et al. "Fluorescence correlation spectroscopy and fluorescence cross-correlation spectroscopy." Wiley Interdiscip Rev Sys Bio Med. 1.2 (2009): 1-15. Print.*

Rossow, et al. "Raster image correlation spectroscopy in live cells." Nat Protoc. 5.11 (2010): 1761-1774. Print.*

Digman et al. "Measuring Fast Dynamics in Solutions and Cells with a Laser Scanning Microscope." Biophysical Journal. 89. (2005): 1317-1327. Print.*

Hou, et al. "A Background Reconstruction Algorithm based on Pixel Intensity Classification in Remote Video Surveillance System." 7th International Conference on Information Fusion. (2004): 1-6. Print.*

Gratton, "Fluorescence correlation spectroscopy and fluorescence cross-correlation spectroscopy." Wiley Interdiscip Rev Sys Bio Med. 1.2 (2009): 1-15. Print.*

Cucchiara, R. et al, "Detecting Moving Objects, Ghosts, and Shadows in Video Streams", IEEE Transactions on Pattern Analysis and Machine Intelligence, IEEE Computer Society, USA, vol. 25, No. 10, Oct. 1, 2003, pp. 1337-1342.

Extended European Search Report, dated Sep. 4, 2014, issued in corresponding European Patent Application No. 10858965.6.

Japanese Office Action, mailed Aug. 20, 2013, issued in corresponding Japanese Patent Application No. 2009-163992.

International Preliminary Report on Patentability, mailed May 23, 2013, issued in corresponding International Application No. PCT/JP2010/069365.

M. Digman, et al., "Measuring Fast Dynamics in Solutions and Cells with a Laser Scanning Microscope," Biophysical Journal 89: 1317-1327 (Aug. 2005).

M. Digman, et al., "Fluctuation Correlation Spectroscopy with a Laser-Scanning Microscope: Exploiting the Hidden Time Structure," Biophysical Journal: Biophysical Letters, L33-L36 (2005).

International Search Report, dated Feb. 8, 2011, issued in corresponding International Application No. PCT/JP2010/069365.

Z. Hou et al., "A Background Reconstruction Algorithm Based on Pixel Intensity Classification," Journal of Software 16 (9): 1568-1576, 2005.

Chinese Office Action, dated May 11, 2015, issued in corresponding Chinese Patent Application No. 201080069838.6.

* cited by examiner

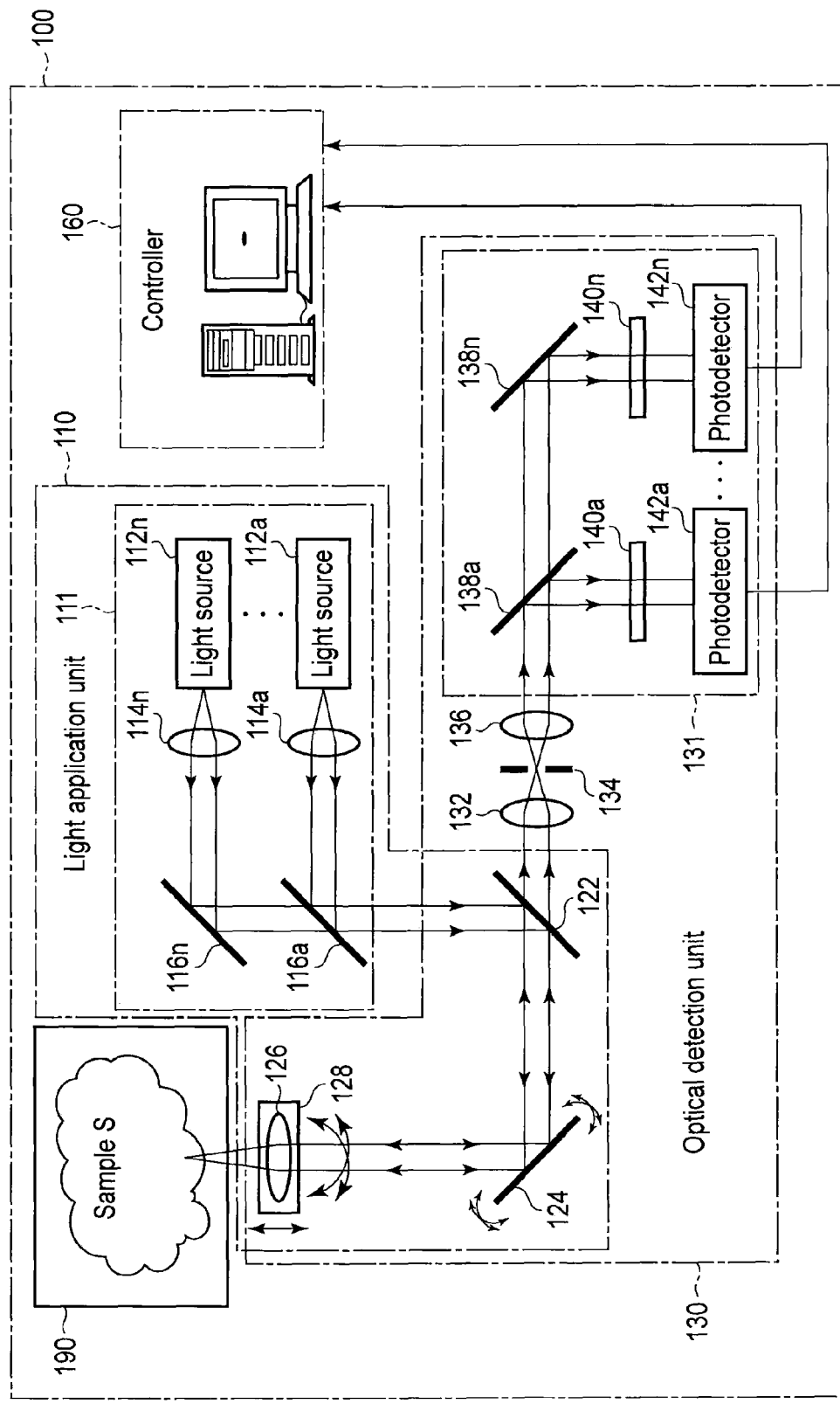
F I G. 1

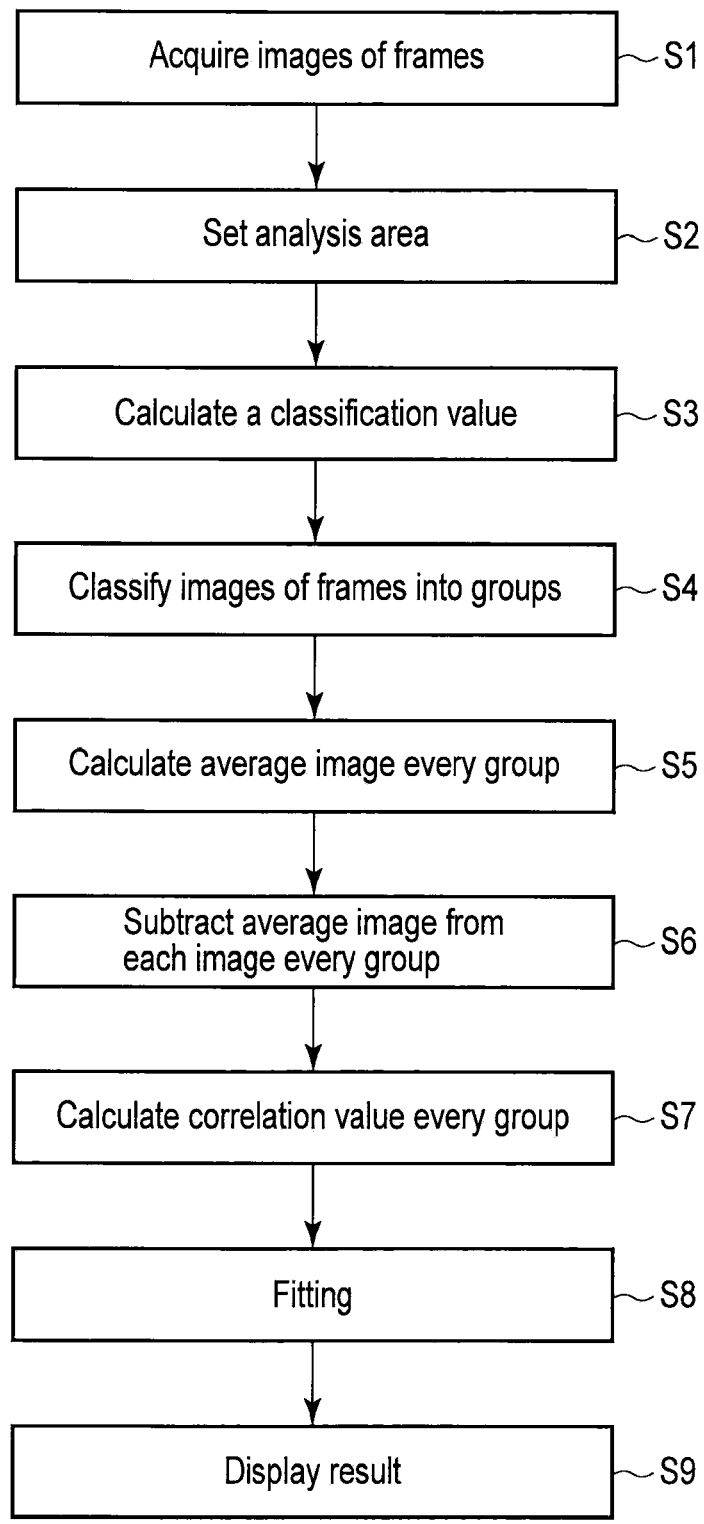
F I G. 3

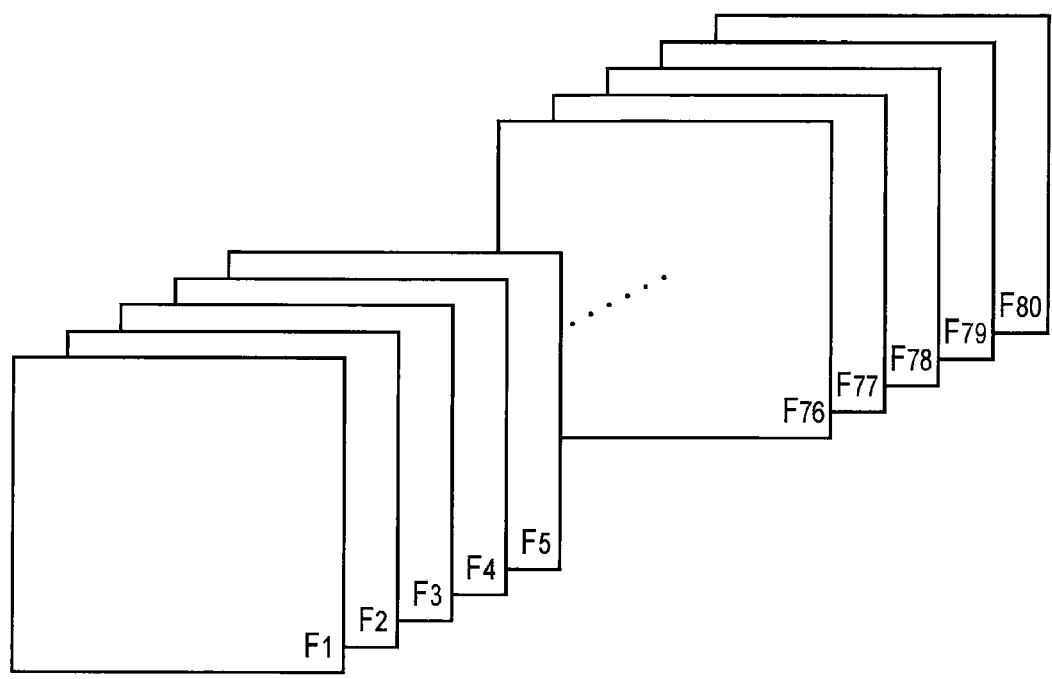
F I G. 4
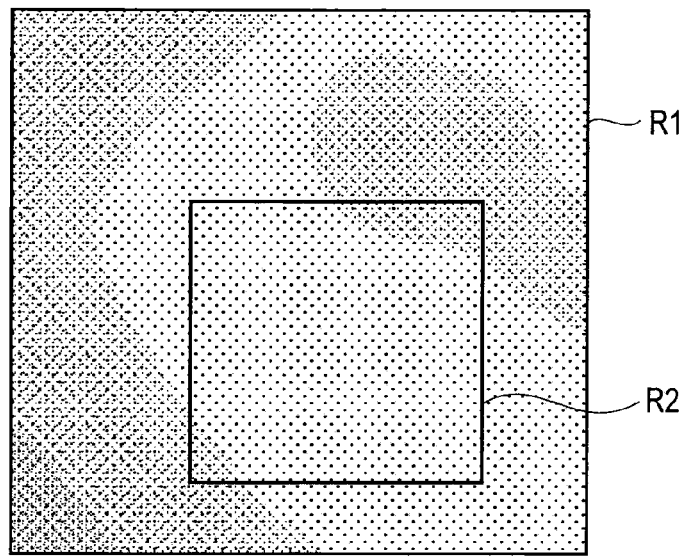
F I G. 5

FIG. 6

F I G. 7
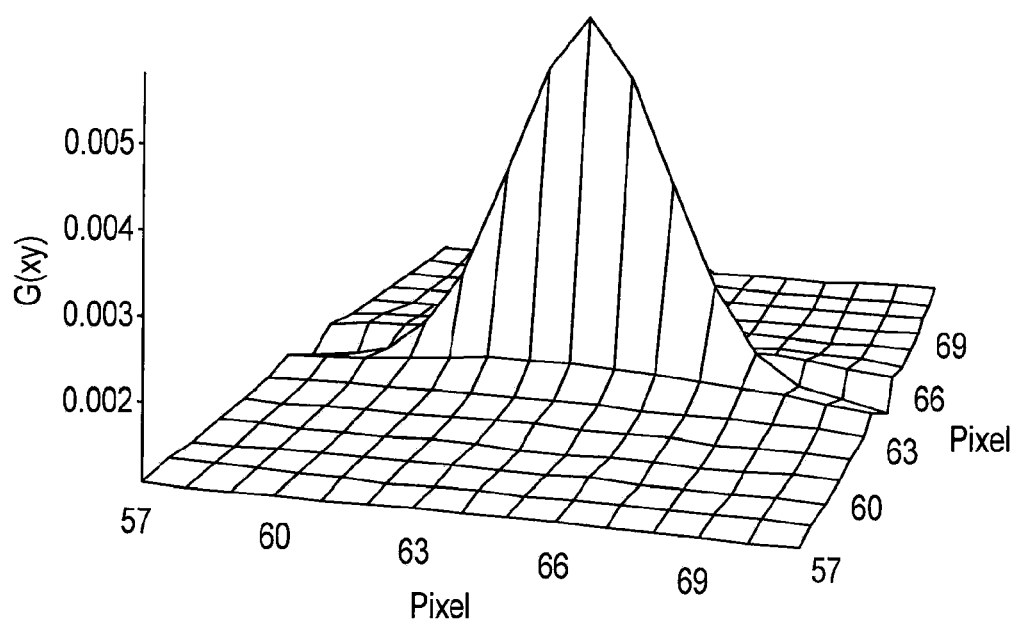
F I G. 8

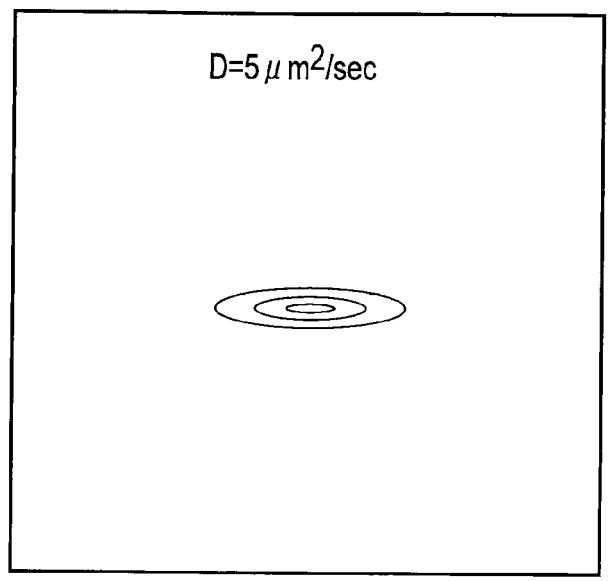
F I G. 9
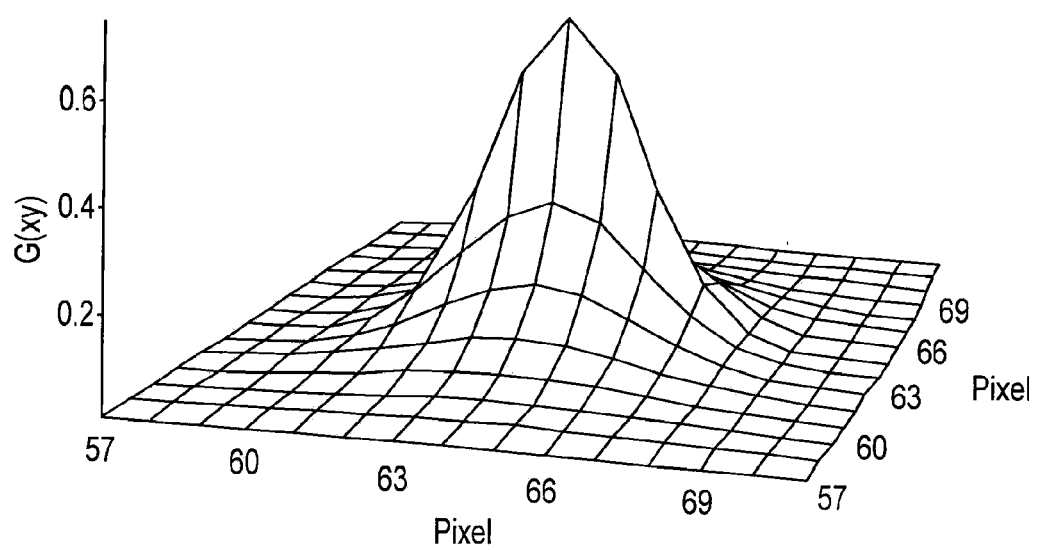
F I G. 10

IMAGE ANALYSIS METHOD AND IMAGE ANALYSIS DEVICE

CROSS-REFERENCE TO RELATED APPLICATIONS

This application is a Continuation Application of PCT Application No. PCT/JP2010/069365, filed Oct. 29, 2010.

BACKGROUND OF THE INVENTION

1. Field of the Invention

The present invention relates to an image analysis method and an image analysis device.

2. Description of the Related Art

Heretofore, as a raster image correlation spectroscopy (RICS), such methods as shown in Non-Patent Literatures 1 and 2 have been suggested. Each of these image analysis methods acquires a fluorescent image comprising raster-scanned images of one or more frames. That is, for a sample to be subjected to image analysis, an interesting area is determined, and this area is repeatedly scanned in a raster scanning system to acquire an image comprising fluorescence intensities of the frames. The fluorescence intensities in the frames are represented as data per pixel unit.

Here, in the sample subjected to the image analysis, large molecules and small molecules are mixed. In such a case, when the small molecules are to be subjected to the image analysis in the sample, it is necessary to remove influences of the large molecules.

PRIOR ART DOCUMENT

Non-Patent Documents

Non-Patent Document 1: "Measuring Fast Dynamics in Solutions and Cells with a Laser Scanning Microscope", Michelle A. Digman, Claire M. Brown, Parijat Sengupta, Paul W. Wiseman, Alan R, Horwitz, and Enrico Gratton, Biophysical Journal, Vol. 89, P1317 to 1327, August 2005.

Non-Patent Document 2: "Fluctuation Correlation Spectroscopy with a Laser-Scanning Microscope: Exploiting the Hidden Time Structure", Michelle A. Digman, Parijat Sengupta, Paul W. Wiseman, Claire M. Brown, Alan R. Horwitz, and Enrico Gratton, Biophysical Journal: Biophysical Letters, L33 to 36, 2005.

SUMMARY OF THE INVENTION

Technical Problem

As shown in Non-Patent Documents 1 and 2, an average method has been suggested as a technique to remove influences of large molecules, immobile molecules, and the like. In the average method, an average image of acquired frame data is calculated, and the calculated image is subtracted from the original frame data. The average image is calculated from continuous part or all of acquired frames regardless of whether the influences of the large molecules or the immobile molecules are included in the frame data. Therefore, the influences of the large molecules or the immobile molecules are removed by the subtraction processing of the same average image regardless of change of the frame data.

Here, when common large or immobile molecules are present in all of the acquired images, the average image of the acquired frame data may be subtracted from each of all the images.

However, in part of all the acquired images, the large or immobile molecules common to the other images are not present sometimes. In this case, first of all, the large molecules or the immobile molecules are not present in the part of the images, and hence it is not suitable to subtract the average image of the acquired frame data from the part of the images. Therefore, according to the methods shown in Non-Patent Documents 1 and 2, for the influences of the large molecules or the immobile molecules, the right removal in the right place (the subtraction of the average image) processing is not performed.

An object of the present invention is to provide an image analysis method of RICS to remove influences of large molecules or immobile molecules suitably in a right place.

Solution to Problem

An image analysis method according to the present invention comprises an image acquiring step of acquiring, in time-series, images of frames comprising pixels in which pixel data of the respective images are acquired in time-series, an analysis area setting step of setting analysis areas to the images, a classification value calculating step of calculating a classification value of each of the analysis areas, a classifying step of classifying the images into one or more groups on the basis of the classification value, an average image calculating step of calculating an average image of the analysis area every group, a new image calculating step of subtracting the average image from each image of the analysis area every group to calculate a new image of the analysis area, and a calculation step of calculating a correlation value on the basis of the new images every group.

Advantageous Effects of the Invention

An image analysis method of RICS is provided to remove influences of large molecules or immobile molecules suitably in a right place.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 schematically shows an image analysis device according to an embodiment of the present invention;

FIG. 3 is a flowchart of image analysis according to the embodiment of the present invention;

FIG. 4 shows fluorescent images of frames acquired in time-series;

FIG. 5 shows an observation area and an analysis area;

FIG. 6 schematically shows the fluorescent images of the frames classified into groups;

FIG. 7 is an image in which a calculation result of a space correlation value by RICS to small molecules is represented by a luminance;

FIG. 8 shows a fitting result of the space correlation value by the RICS to the small molecules;

FIG. 9 is an image in which a calculation result of a space correlation value by the RICS to large molecules is represented by the luminance; and FIG. 10 shows a fitting result of the space correlation value by the RICS to the large molecules.

DESCRIPTION OF EMBODIMENTS

Figure 2:
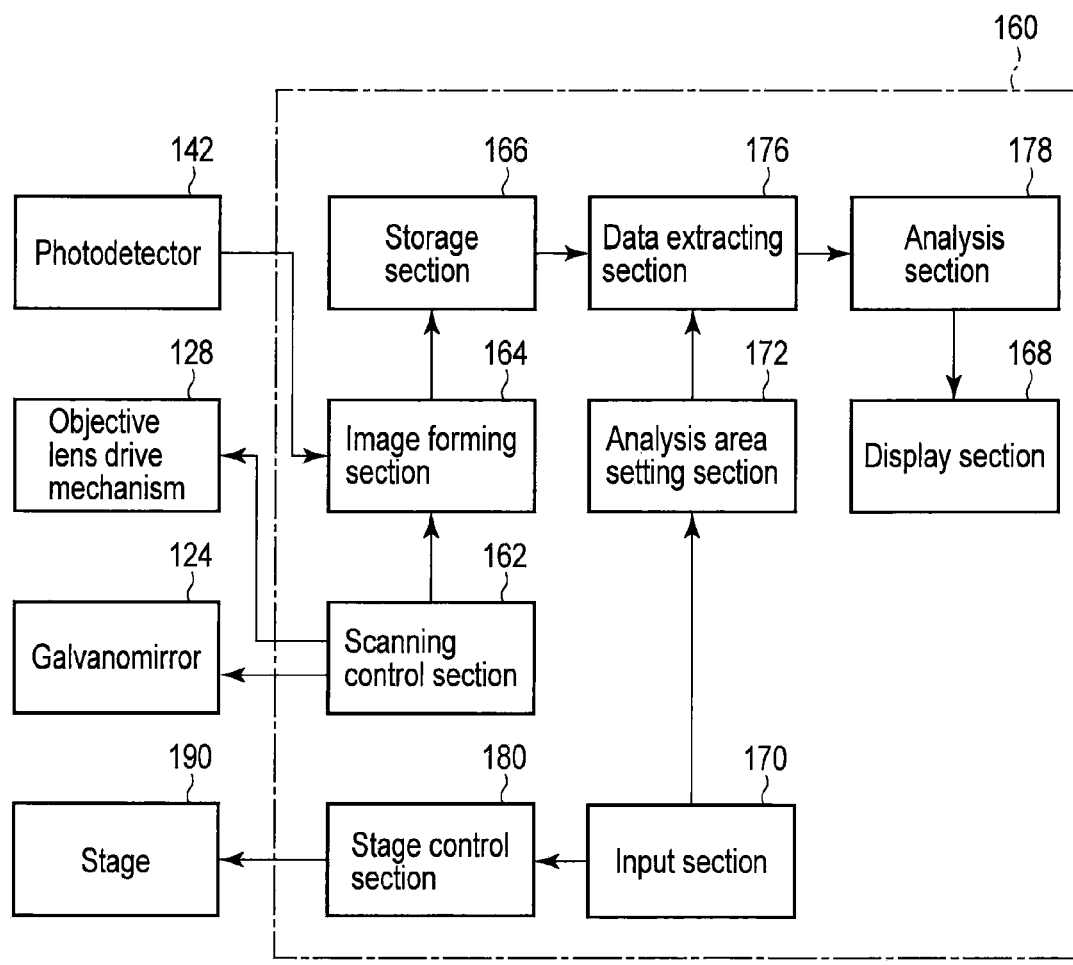
FIG. 2 shows function blocks of a controller shown in FIG. 1.

Hereinafter, embodiments of the present invention will be described with reference to the drawings.

FIG. 1 schematically shows an image analysis device according to the embodiment of the present invention. This image analysis device is constituted on the basis of a scanning type confocal optical microscope for fluorescence observation of a sample.

As shown in FIG. 1, an image analysis device 100 has a light application unit 110 to apply an excitation light to a sample S, an optical detection unit 130 to detect light emitted from a point of measurement in the sample S, a controller 160 to execute control required for image analysis, and a sample stage 190 to support the sample S.

The sample S is contained in a sample container such as a micro plate or a slide glass, and mounted on the sample stage 190. The sample stage 190 supports, for example, the sample S so that the sample is movable to the light application unit 110 and the optical detection unit 130 in a lateral direction (the xy direction) and a height direction (the z direction). For example, the sample stage 190 includes three stepping motors in which output shafts are perpendicular to one another, so as to move the sample S in the xyz-direction by these stepping motors.

The image analysis device 100 is a multiplex light application/multiplex light detection type. Therefore, the light application unit 110 includes a light source system 111 of n channels, and in accordance with this system, the optical detection unit 130 includes a detection system 131 of the n channels. The detection system 131 of the n channels detects fluorescence light generated by the excitation light emitted from the light source system 111 of the n channels, respectively. Here, the n channels comprises channel 1, channel 2, . . . , and channel n. The channels vary in accordance with types of the excitation light, respectively.

The n-channel light source system 111 of the light application unit 110 includes light sources 112a, . . . , 112n, collimating lenses 114a, . . . , 114n, and dichroic mirrors 116a, . . . , 116n. The light sources 112a, . . . , 112n emit the excitation light for exciting fluorescent dyestuffs included in the sample S to cause it to emit the light (the fluorescence light) from the sample S. Wavelengths of the excitation light emitted from the light sources 112a, . . . , 112n are different from one another in accordance with types of the fluorescent dyestuffs included in the sample S. The light sources 112a, . . . , 112n comprise, for example, laser light sources of oscillation wavelengths that match the fluorescent dyestuffs in the sample S. The collimating lenses 114a, . . . , 114n collimate the excitation light emitted from the light sources 112a, . . . , 112n, respectively. The dichroic mirrors 116a, . . . , 116n reflect the excitation light that has passed through the collimating lenses 114a, . . . , 114n in the same direction, respectively. The dichroic mirrors 116a, . . . , 116n transmit the excitation light incoming from the upper side of FIG. 1, and reflect the excitation light incoming from the right side of FIG. 1, respectively. As a result, the excitation light of the different wavelengths emitted from the light sources 112a, . . . , 112n, respectively, pass through the dichroic mirror 116a and are then combined into a beam. Since the dichroic mirror 116n does not need to transmit the excitation light, it may be replaced with a simple mirror.

The light application unit 110 further includes a dichroic mirror 122, a galvanomirror 124, an objective lens 126 and an objective lens drive mechanism 128. The dichroic mirror 122 reflects the excitation light from the light source system 111 toward the galvanomirror 124, and transmits the fluorescence light emitted from the sample S. The galvanomirror 124 reflects the excitation light toward the objective lens 126, and changes a reflecting direction of the excitation light. The objective lens 126 converges the excitation light to apply it to the point of measurement in the sample S, and takes in the light from the point of measurement in the sample S. In the objective lens 126, a lens having a large NA (numerical aperture) is used for formation of a micro confocal area (the point of measurement). A size of the confocal area obtained by this lens is a diameter of about 0.6 μm and a length of about 2 μm of a substantially cylindrical area. The galvanomirror 124 constitutes xy scanning means for scanning the point of measurement in the xy direction. The xy scanning means is constituted by using a galvanomirror, but may be constituted by using an acoustooptic modulation element (AOM), a polygon mirror, a hologram scanner or the like. The objective lens drive mechanism 128 moves the objective lens 126 along an optical axis. In consequence, the point of measurement is moved in the z direction. That is, the objective lens drive mechanism 128 constitutes z scanning means for scanning the point of measurement in the z direction.

The optical detection unit 130 shares the objective lens 126, the galvanomirror 124 and the dichroic mirror 122 with the light application unit 110. The optical detection unit 130 further includes a converging lens 132, a pinhole 134 and a collimating lens 136. The converging lens 132 converges the light transmitted through the dichroic mirror 122. The pinhole 134 is disposed at a focal point of the converging lens 132. That is, the pinhole 134 is at a position that is conjugate with the point of measurement in the sample S, and selectively transmits the only light from the point of measurement. The collimating lens 136 collimates the light that has passed through the pinhole 134. The light that has passed through the collimating lens 136 enters the detection system 131 of the n channels.

The detection system 131 of the n channels includes dichroic mirrors 138a, . . . , 138n, fluorescence filters 140a, . . . , 140n, and photodetectors 142a, . . . , 142n.

The dichroic mirrors 138a, . . . , 138n selectively reflect the light of wavelengths near a wavelength region of the fluorescence light that is generated from the sample S by the excitation light from the light sources 112a, . . . , 112n, respectively. The dichroic mirror 138n does not need to transmit the light, and hence may be replaced with a simple mirror. The fluorescence filters 140a, . . . , 140n interrupt the light of undesirable wavelength components from the light reflected by the dichroic mirrors 138a, . . . , 138n, respectively, and selectively transmit the only fluorescence light generated by the excitation light from the light sources 112a, . . . , 112n. The fluorescence light transmitted through the fluorescence filters 140a, . . . , 140n enter the photodetectors 142a, . . . , 142n, respectively. The photodetectors 142a, . . . , 142n output signals corresponding to intensities of the incident light. That is, the photodetectors 142a, . . . , 142n output fluorescence intensity signals from the point of measurement in the sample S.

The controller 160 is constituted of, for example, a personal computer. The controller 160 acquires, stores and displays a fluorescent image of an observation area of the sample S, waits for input of setting of the number of frames (the frame number) of the fluorescent image to be acquired, or an analysis area, and performs the image analysis (the calculation of a correlation value), estimation of a diffusion time, and the like. Moreover, the controller 160 executes control of the galvanomirror 124, which is the xy scanning means, the objective lens drive mechanism 128, which is the z scanning means, the sample stage 190 and the like.

Function blocks of the controller shown in FIG. 1 are shown in FIG. 2. As shown in FIG. 2, the controller 160 includes a scanning control section 162, an image forming section 164, a storage section 166, a display section 168, an input section 170, an analysis area setting section 172, a data extracting section 176, an analysis section 178 and a stage control section 180. An image acquisition unit is constituted by the scanning control section 162, the image forming section 164, the storage section 166, the stage control section 180, the galvanomirror 124, the objective lens drive mechanism 128, the sample stage 190, and the photodetectors 142.

The scanning control section 162 controls the galvanomirror 124 so that an application position of the excitation light is raster-scanned with respect to the sample S, when the fluorescent image of the sample S is acquired. Moreover, if necessary, the scanning control section 162 controls the objective lens drive mechanism 128 so that the application position of the excitation light is z-scanned with respect to the sample S. The image forming section 164 forms the fluorescent image of the sample S from information of the application position of the excitation light, which is input from the scanning control section 162, and the output signals of the photodetectors 142a, ..., 142n. In consequence, the fluorescent image can be acquired. The storage section 166 successively stores the fluorescent images formed by the image forming section 164. The display section 168 displays the fluorescent image of the sample S, or the analysis result. The input section 170 includes, for example, a mouse, and a keyboard, and cooperates with the display section 168 to constitute a GUI. This GUI is used in setting of the number of the frames to be acquired, the observation area or the analysis area, or the like. The stage control section 180 controls the sample stage 190 in accordance with input information from the input section 170 to set, for example, the observation area. The analysis area setting section 172 sets the analysis area in accordance with the input information from the input section 170. The data extracting section 176 extracts necessary data from the fluorescent image stored in the storage section 166 on the basis of the input information from the analysis area setting section 172. The necessary data may be, for example, all the pixel data of all the fluorescent images stored in the storage section 166 or part of the pixel data, or the data may be all the pixel data or part of the pixel data of part of the fluorescent images stored in the storage section 166. The analysis section 178 calculates the correlation values of the data extracted by the data extracting section 176 as described later. More specifically, the analysis section 178 calculates a classification value of analysis areas as described later, and classifies the fluorescent images into one or more groups on the basis of the classification value. The analysis section 178 then calculates an average image of the analysis areas every group, and subtracts the average image from each image of the analysis area to calculate a new image of the analysis area every group. Afterward, the analysis section 178 calculates correlation value on the basis of the new images every group.

In FIG. 1, the excitation light emitted from the light sources 112a, ..., 112n passes through the collimating lenses 114a, ..., 114n, the dichroic mirrors 116a, ..., 116n, the dichroic mirror 122, the galvanomirror 124, and the objective lens 126, to be applied to the point of measurement in the sample S. The point of measurement at which the excitation light is applied is raster-scanned in the xy direction by the galvanomirror 124. Furthermore, if necessary, the point of measurement is z-scanned by the objective lens drive mechanism 128. The sample S that has received the excitation light emits the fluorescence light from the point of measurement. The light from the sample S (including an undesirable reflected light and the like in addition to the fluorescence light) reach the pinhole 134 through the objective lens 126, the galvanomirror 124, the dichroic mirror 122, and the converging lens 132. Since the pinhole 134 is at the position that is conjugate with the point of measurement, the only light from the point of measurement in the sample S passes through the pinhole 134. The light that has passed through the pinhole 134, i.e., the light from the point of measurement in the sample S enters the detection system 131 of the n channels through the collimating lens 136. The light that has entered the detection system 131 of the n channels are separated (i.e., diffracted) in accordance with the wavelengths by the dichroic mirrors 138a, ..., 138n, and the undesirable components are removed by the fluorescence filters 140a, ..., 140n. As a result, the only fluorescence light generated by the excitation light from the light sources 112a, ..., 112n enters the photodetectors 142a, ..., 142n, respectively. The photodetectors 142a, ..., 142n output the fluorescence intensity signals indicating intensities of the incident light, i.e., the fluorescence light emitted from the point of measurement in the sample 5, respectively. The fluorescence intensity signals are input into the image forming section 164. The image forming section 164 processes the input fluorescence intensity signal synchronously with positional information of the xy direction (and the z direction) every raster scanning (and z scanning) time, to form the fluorescent image of one frame of a focal plane (a flat plane or a curved plane to which the point of measurement has moved) in the sample S. The formed fluorescent image is stored in the storage section 166. A series of operations mentioned herein are repeated as much as the set number of the frames to be acquired, and the fluorescent images corresponding to the set number of the frames are acquired. The respective fluorescent images comprise the pixels in which the pixel data are acquired in time-series.

The fluorescent images stored in the storage section 166 are processed as required, and displayed in the display section 168. For example, it is possible that the fluorescent images of the frames are acquired while changing the z position of the point of measurement, and then synthesized to form a three-dimensional image, which is displayed in the display section 168.

Hereinafter, a procedure of the image analysis will be described with reference to FIG. 3. Moreover, the respective steps will be described suitably with reference to FIG. 4 to FIG. 6.

<Step S1>:

The observation area of the sample S and the number of the frames of the fluorescent images to be acquired are set. The fluorescent images of the set observation area are acquired as much as the set number of the frames. The acquisition of the fluorescent images is performed for the same observation area by the same scanning method. The acquired fluorescent images of the frames are the images acquired in time-series, and each of the images comprises pixels in which pixel data are acquired in time-series.

The fluorescent images of the frames acquired in time-series are schematically shown in FIG. 4. In FIG. 4, $F_n$ indicates the fluorescent image of the n-th frame in one channel. That is, FIG. 4 shows an example where the fluorescent images of 80 frames have been acquired.

<Step S2>:

As shown in FIG. 5, an area to be analyzed (the analysis area) R2 is set to an area (the observation area) R1 of the acquired fluorescent image. The analysis area R2 is not limited to a part of the observation area R1, and may coincide with the observation area R1. The analysis area R2 is set to the observation area R1, i.e., the scanned area in the step S1, by default in an application. When the whole observation area R1 is analyzed, this step is not required.

<Step S3>:

A classification value of the analysis area R2 is calculated. The classification value is, for example, a statistic value of the pixel data of the analysis area R2, and is one of a maximum value, a minimum value, an average value, a relative difference, and a relative ratio of the pixel data of the analysis area R2. The pixel data are, for example, fluorescence intensities obtained from a two-dimensional or three-dimensional observation area. The relative difference is, for example, a difference between the maximum value and the minimum value.

In the following description, the classification value of the analysis area of each of fluorescent images $F_1, \ldots, F_{20}$ is $D_a$, the classification value of the analysis area of each of fluorescent images $F_{21}, \ldots, F_{50}$ is $D_b$, which is noticeably different from $D_a$, and the classification value of the analysis area of each of fluorescent images $F_{51}, \ldots, F_{80}$ is $D_a$.

<Step S4>:

The images are classified into one or more groups on the basis of the classification value. For example, the images are divided into groups before and after the classification value noticeably changes. The number of the groups is determined in accordance with a way of the change of the classification value.

Figure 6:
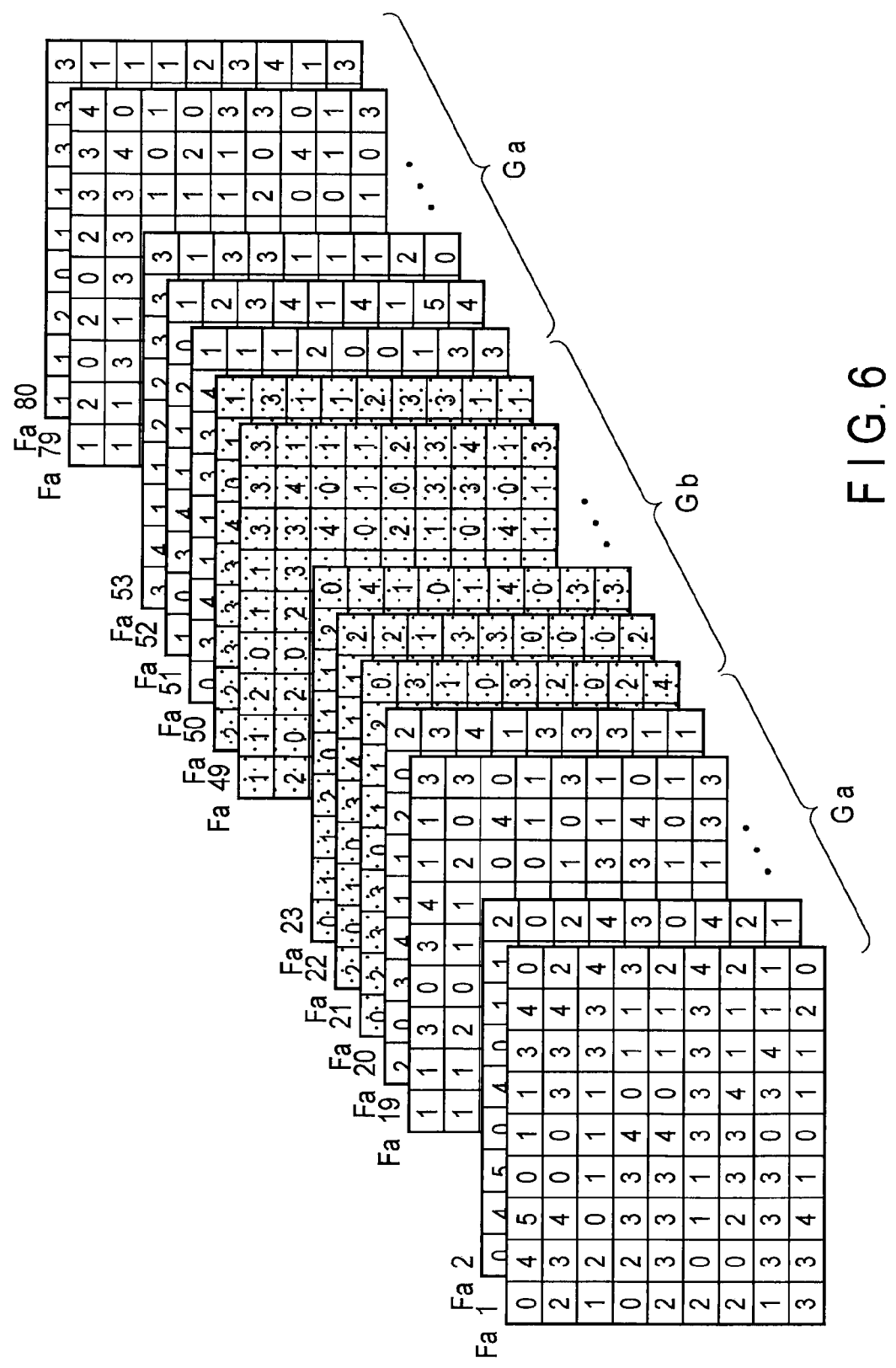

The fluorescent images of the analysis areas of the frames classified into the groups are schematically shown in FIG. 6. In FIG. 6, $Fa_n$ indicates the image of the analysis area of the fluorescent image of the n-th frame. FIG. 6 shows an example where images $Fa_1, \ldots, Fa_{80}$ of the analysis areas of the fluorescent images $F_1, \ldots, F_{80}$ shown in FIG. 4 are classified into two groups $G_a$ and $G_b$. In FIG. 6, the images $Fa_1, \ldots, Fa_{20}$ and the images $Fa_{51}, \ldots, Fa_{80}$ are classified into the group $G_a$, and the images $Fa_{21}, \ldots, Fa_{50}$ are classified into the group $G_b$.

<Step S5>:

An average image of the analysis areas is calculated every group. The average image may be an average value of all the images included in each group, or an average value of part of the images included in each group. For example, in the calculation of the average image, the number of the images included in each group is calculated, and the average image of each group is calculated on the basis of the calculated number of the images.

More specifically, for all the images included in each group, an average value of the pixel data is calculated every pixel constituting the analysis area. Then, the image comprising the average value of each pixel data calculated every pixel may be obtained as the average image.

In the following description, the average image of the images $Fa_1, \ldots, Fa_{20}$ and the images $Fa_{51}, \ldots, Fa_{80}$ included in the group $G_a$ is $A_a$, and the average image of the images $Fa_{21}, \ldots, Fa_{50}$ included in the group $G_b$ is $A_b$.

In place of calculating one average image $A_a$ from the images $Fa_1, \ldots, Fa_{20}$ and the images $Fa_{51}, \ldots, Fa_{80}$, an average image $A_{a1}$ may be calculated from the images $Fa_1, \ldots, Fa_{20}$, and another average image $A_{a2}$ may be calculated from the images $Fa_{51}, \ldots, Fa_{80}$.

<Step S6>:

The average image is subtracted from each image of the analysis area to calculate a new image of the analysis area every group. Here, to subtract the average image from each image of the analysis area, for example, the pixel data of the average image may be subtracted from the pixel data of each image, to obtain the image comprising the calculated value, every pixel constituting the analysis area.

The new image of the analysis area of the n-th frame is $Fb_n$. For the images $Fa_1, \ldots, Fa_{20}$ and $Fa_{51}, \ldots, Fa_{80}$ included in the group $G_a$, new images $Fb_1, \ldots, Fb_{20}$ and $Fb_{51}, \ldots, Fb_{80}$ are calculated in accordance with $Fb_1 = Fa_1 - A_a, \ldots, Fb_{20} = Fa_{20} - A_a, Fb_{51} = Fa_{51} - A_a, \ldots, Fa_{51} = Fa_{20} - A_a$, and for the images $Fa_{21}, \ldots, Fa_{50}$ included in the group $G_b$, new images $Fb_{21}, \ldots, Fb_{50}$ are calculated in accordance with $Fb_{21} = Fa_{21} - A_b, \ldots, Fb_{50} = Fa_{50} - A_b$.

To calculate the new images $Fb_1, \ldots, Fb_{20}$ and $Fb_{51}, \ldots, Fb_{80}$, in place of subtracting the common $A_a$ from each of the images $Fa_1, \ldots, Fa_{20}$ and $Fa_{51}, \ldots, Fa_{80}$, the above-mentioned average image $A_{a1}$ may be subtracted from each of the images $Fa_1, \ldots, Fa_{20}$, and the above-mentioned average image $A_{a2}$ may be subtracted from each of the images $Fa_{51}, \ldots, Fa_{80}$.

<Step S7>:

A correlation value is calculated on the basis of the new images every group. Each pixel data for use in the calculation of the correlation value may be the data of the pixel itself, or a statistic value of the data of pixels including the pixel. The pixels may be, for example, the pixel of attention and the pixel adjacent to this pixel of attention. The statistic value may be, for example, one of an average value, a maximum value, a minimum value, a relative difference, an absolute difference, and a relative ratio of the pixel data. Which statistic value to be used is determined by judging which information is to be obtained by the analysis of RICS.

In the calculation of the correlation value, for example, the minimum value of the pixel data is calculated every group, the calculated minimum value is added to the pixel data of all the new images, and the correlation value is calculated for the new images to which the minimum value has been added. According to this processing, all the pixel data of the new images become positive. Here, there has been described an example where the minimum value is added so that all the pixel data of the new images are made to be positive, but the value to be added is not limited to the minimum value, and any value that is larger than the minimum value may be added.

Further in the calculation of the correlation value, each of the images may be reconstituted on the basis of the pixel data, and the correlation value of the reconstituted images may be calculated. For example, the data of the adjacent pixels are added up, to set the number of the pixel data to half. Alternatively, one pixel datum is divided into a plurality of data. Under normal circumstances, once the image is acquired, the number of the pixel data does not increase. However, it is supposed that an intensity of the acquired pixel data spreads around the pixel data in Gaussian distribution, to compensate for the pixel data that cannot originally be acquired. The number of the pixel data essentially does not increase, but visual effects improve.

In the calculation of the correlation value, for example, a space auto-correlation value is calculated by using the following Equation (1):

$$G_{sa}(\xi, \psi) = \frac{\Sigma I(x, y) * I(x+\xi, y+\psi)/M_{11}}{(\Sigma I(x, y)/M_1)^2} \quad (1)$$

where $G_{sa}$ is the space auto-correlation value of the RICS, I is the pixel data, x and y are spatial coordinates of a measurement point, $\xi$ and $\psi$ are change amounts of the spatial coordinates from the measurement point, $M_{11}$ is the number of data product sum calculation times, and $M_1$ is the total number of the data.

Alternatively, in the calculation of the correlation value, for example, a space cross-correlation value is calculated by using the following Equation (2):

$$G_{sc}(\xi, \psi) = \frac{\Sigma I_1(x, y) * I_2(x+\xi, y+\psi)/M_{12}}{(\Sigma I_1(x, y)/M_1) * (\Sigma I_2(x, y)/M_2)} \quad (2)$$

where $G_{sc}$ is the space cross-correlation value of the RICS, $I_1$ is the pixel data of the channel 1, $I_2$ is the pixel data of the channel 2, x and y are the spatial coordinates of the measurement point, $\xi$ and $\psi$ are the change amounts of the spatial coordinates from the measurement point, $M_{12}$ is the number of the data product sum calculation times, $M_1$ is the total number of the data of the channel 1, and $M_2$ is the total number of the data of the channel 2. The Equation (2) is a calculating equation of the space cross-correlation value between the channel 1 and the channel 2, but the channels may suitably be changed.

Furthermore, the correlation values calculated on the basis of the respective new images are averaged.

The correlation value calculated on the basis of the new image $Fb_n$ of the analysis area of the n-th frame is $G_{sn}$. Then, an average correlation value $G_s$ is calculated in accordance with $G_s = (G_{s1} + G_{s2} + \ldots + G_{s79} + G_{s80})/80$.

<Step S8>

Fitting of the calculation result of the space correlation value of the above step S7 is performed in accordance with the following Equation (3):

$$G_s(\xi, \psi) = S(\xi, \psi) * G(\xi, \psi) \quad (3)$$

$$S(\xi, \psi) = \exp\left(-\frac{\frac{1}{2} * \left[\left(\frac{2\xi\delta_r}{W_0}\right)^2 + \left(\frac{2\psi\delta_r}{W_0}\right)^2\right]}{\left(1 + \frac{4D(\tau_p\xi + \tau_l\psi)}{W_0^2}\right)}\right)$$

$$G(\xi, \psi) = \frac{\gamma}{N}\left(\left(1 + \frac{4D(\tau_p\xi + \tau_l\psi)}{W_0^2}\right)^{-1} * \left(1 + \frac{4D(\tau_p\xi + \tau_l\psi)}{W_z^2}\right)^{-\frac{1}{2}}\right)$$

where $G_s$ is the space correlation value of the RICS, S is an influence of the scanning in the analysis of the RICS, G is an influence of time delay in the analysis of the RICS, D is a diffusion constant, $\xi$ and $\psi$ are the change amounts of the spatial coordinates from the measurement point, $\delta_r$ is a pixel size, N is the number of molecules, $W_0$ is a radius of an excitation laser beam in a lateral direction, $W_z$ is a radius of the excitation laser beam in a vertical direction, $\tau_p$ is a pixel time, $\tau_l$ is a line time, and $\gamma$ is an arbitrary constant.

It is to be noted that $\gamma$ can suitably be set in accordance with the system. For example, the fitting may be performed by using $\gamma = 1$.

Moreover, the pixel time means a deviation in acquisition time between the pixels. Moreover, the line time means a deviation in acquisition time between the first pixel of any line and the first pixel of the next line. That is, the line time means the time required to scan one line.

The fitting is performed in this way by use of the Equation (3), to estimate the diffusion time. Specifically, the correlation value $G_{sa}$ or the correlation value $G_{sc}$ to different delay times is obtained by using the Equation (1) or the Equation (2). Here, the delay time means a difference between the acquisition time of one pixel and the acquisition time of another pixel. For example, the delay time between $(\xi, \psi) = (1, 1)$ and $(\xi, \psi) = (4, 2)$ is represented by $(4-1)\tau_p + (2-1)\tau_l$.

Here, in the Equation (3), when the delay time is zero, ($\xi = 0$, $\gamma = 0$), S is 1, and $G_s$ is represented by $1/N$. Therefore, the number of the molecules can be obtained. This is newly substituted into the Equation (3).

Then, the suitable diffusion constant D is obtained by causing a difference between the correlation value $G_{sa}$ or the correlation value $G_{sc}$ obtained as the measured value and $G_s$ obtained as a theoretical value to be minimum while varying the diffusion constant D, which is an unknown value. Consequently, the fitting in accordance with the Equation (3) is to estimate the most suitable molecule number or diffusion constant in the two-dimensional or three-dimensional observation area while varying the diffusion constant D.

Then, the diffusion time can be obtained from the diffusion constant.

That is, a relation between the diffusion constant and the diffusion time is represented by the following Equation (4):

$$\tau = W_0^2/4D \quad (4)$$

where D means the diffusion constant, $\tau$ means the diffusion time, and $W_0$ means the radius of the excitation laser beam in the lateral direction.

<Step S9>:

The analysis result is displayed and suitably stored. Specifically, the calculation result of the space correlation value obtained in the step S7 and the fitting result of the space correlation value obtained in the step S8 are displayed. An example of the analysis result is shown in FIG. 7 to FIG. 10. FIG. 7 is an image in which the calculation result of the space correlation value to small molecules is represented by a luminance, and FIG. 8 shows a fitting result of the image. Moreover, FIG. 9 is an image in which the calculation result of the space correlation value to large molecules is represented by the luminance, and FIG. 10 shows a fitting result of the image.

Consequently, according to the present embodiment, in spatial correlation analysis in which such image data as in the RICS is used as a calculation base, the images of the frames are classified into several groups in accordance with change of frame data, and the subtraction processing of the average image is performed every group. That is, the subtraction processing of one average image calculated from the frame in which different influences of the large molecules or the immobile molecules are mixed is avoided. The influences of the large molecules or the immobile molecules are classified in advance, and the average image is calculated to perform the subtraction processing every classified group. In consequence, the influences of the large molecules or the immobile molecules are removed by the right method in the right place, every group in accordance with the change of the frame data.

Hitherto, the embodiments of the present invention have been described with reference to the drawings, but the present invention is not limited to these embodiments, and various modifications and alterations may be made without departing from the scope of the present invention.

Moreover, in the embodiments, the image acquired by the raster scanning has been described, but the image is not limited to the image acquired by the raster scanning, and may be an image comprising pixels in which pixel data are acquired in time-series, or an image acquired by another scanning method.

REFERENCE SIGNS LIST

100 . . . image analysis device, 110 . . . light application unit, 112a, . . . , 112n . . . light source, 114a, . . . , 114n . . . collimating lens, 116a, . . . , 116n . . . dichroic mirror, 122 . . . dichroic mirror, 124 . . . galvanomirror, 126 . . . objective lens, 128 . . . objective lens drive mechanism, 130 . . . optical detection unit, 132 . . . convergent lens, 134 . . . pinhole, 136 . . . collimating lens, 138a, . . . , 138n . . . dichroic mirror, 140a, . . . , 140n . . . fluorescence filter, 142a, . . . , 142n . . . photodetector, 160 . . . controller, 162 . . . scanning control section, 164 . . . image forming section, 166 . . . storage section, 168 . . . display section, 170 . . . input section, 172 . . . analysis area setting section, 176 . . . data extracting section, 178 . . . analysis section, 180 . . . stage control section, 190 . . . sample stage, R1 . . . observation area, and R2 . . . analysis area.

What is claimed is:

1. An image analysis method of a scanning type optical microscope to analyze a scanned image acquired by detecting light from a measurement point in a sample mixed with molecules of different sizes and scanning of the measurement point to be detected, comprising:
an image acquiring step of acquiring, in time-series, scanned images of frames comprising pixels in which pixel data of the respective scanned images are acquired in time-series;
an analysis area setting step of setting analysis areas to the scanned images;
a classification value calculating step of calculating a classification value of each of the analysis areas;
a classifying step of classifying the scanned images into two or more groups on the basis of magnitude of change of the classification value;
an average image calculating step of calculating an average image of the analysis area of every group;
a new image calculating step of subtracting the average image from each scanned image of the analysis area of every group to calculate a new image of the analysis area; and
a calculation step of calculating a correlation value by raster-image correlation spectroscopy on the basis of the new images of every group.

2. The image analysis method according to claim 1, wherein the classification value is one of a maximum value, a minimum value, an average value, a relative difference, and a relative ratio of the pixel data of the analysis area.

3. The image analysis method according to claim 1, wherein the pixel data are fluorescence intensities obtained from a two-dimensional or three-dimensional observation area.

4. The image analysis method according to claim 1, wherein the calculation step of calculating a correlation value on the basis of the new images of every group calculates a minimum value of the pixel data in every group, adds the calculated minimum value to the pixel data of all the new images, and calculates the correlation value for the new images to which the minimum value has been added.

5. The image analysis method according to claim 1, wherein the average image calculating step calculates the number of the images included in each group, and calculates the average image of each group on the basis of the calculated number of the images.

6. The image analysis method according to claim 1, wherein the calculation step of calculating a correlation value on the basis of the new images of every group reconstitutes each of the images on the basis of the pixel data of the new images, and calculates the correlation value for the reconstituted images.

7. The image analysis method according to claim 1, wherein the images are obtained by a scanning type microscope.

8. The image analysis method according to claim 1, wherein the calculation step of calculating a correlation value on the basis of the new images of every group performs correlating calculation of a two-dimensional or three- dimensional observation area by use of the following Equation (1) or the following Equation (2):

$$G_{sa}(\xi, \psi) = \frac{\Sigma I(x, y) * I(x+\xi, y+\psi)/M_{11}}{(\Sigma I(x, y)/M_1)^2} \quad (1)$$

where $G_{sa}$ is a space auto-correlation value of RICS, I is the pixel data, x and y are spatial coordinates of a measurement point, $\xi$ and $\psi$ are change amounts of the spatial coordinates from the measurement point, $M_{11}$ is the number of data product sum calculation times, and $M_1$ is the total number of the data, $$G_{sc}(\xi, \psi) = \frac{\Sigma I_1(x, y) * I_2(x+\xi, y+\psi)/M_{12}}{(\Sigma I_1(x, y)/M_1) * (\Sigma I_2(x, y)/M_2)} \quad (2)$$

where $G_{sc}$ is a space cross-correlation value of the RICS, $I_1$ is the pixel data of channel 1, $I_2$ is the pixel data of channel 2, x and y are the spatial coordinates of the measurement point, $\xi$ and $\psi$ are the change amounts of the spatial coordinates from the measurement point, $M_{12}$ is the number of the data product sum calculation times, $M_1$ is the total number of the data of the channel 1, and $M_2$ is the total number of the data of the channel 2.

9. The image analysis method according to claim 8, wherein the calculation step of calculating a correlation value on the basis of the new images of every group performs fitting of the calculation result of the space correlation value by use of the following Equation (3):

$$G_s(\xi, \psi) = S(\xi, \psi) * G(\xi, \psi) \quad (3)$$

$$S(\xi, \psi) = \exp\left(-\frac{\frac{1}{2} * \left[\left(\frac{2\xi\delta_r}{W_0}\right)^2 + \left(\frac{2\psi\delta_r}{W_0}\right)^2\right]}{\left(1 + \frac{4D(\tau_p\xi + \tau_l\psi)}{W_0^2}\right)}\right)$$

$$G(\xi, \psi) = \frac{\gamma}{N}\left(\left(1 + \frac{4D(\tau_p\xi + \tau_l\psi)}{W_0^2}\right)^{-1} * \left(1 + \frac{4D(\tau_p\xi + \tau_l\psi)}{W_z^2}\right)^{-\frac{1}{2}}\right)$$

where $G_s$ is the space correlation value of the RICS, S is an influence of the scanning in the analysis of the RICS, G is an influence of time delay in the analysis of the RICS, D is a diffusion constant, $\xi$ and $\psi$ are the change amounts of the spatial coordinates from the measurement point, $\delta_r$ is a pixel size, N is the number of molecules, $W_o$ is a radius of an excitation laser beam in a lateral direction, $W_z$ is a radius of the excitation laser beam in a vertical direction, $\tau_p$ is a pixel time, $\tau_l$ is a line time, and y is an arbitrary constant.

10. A scanning type optical microscope having an image analysis device to analyze a scanned image acquired by detecting light from a measurement point in a sample mixed with molecules of different sizes and scanning the measurement point to be detected, comprising:

image acquiring means to acquire, in time-series, scanned images of frames comprising pixels in which pixel data of the respective scanned images are acquired in time-series;
   analysis area setting means to set analysis areas to the scanned images;
   classification value calculating means to calculate a classification value of each of the analysis areas; and
   calculation means to classify the scanned images into two or more groups on the basis of magnitude of change of the classification value, calculate an average image of the analysis area of every group, subtract the average image from the image of the analysis area to calculate a new image of the analysis area of every group, and calculate a correlation value for the new images by raster-image correlation spectroscopy.

11. The scanning type optical microscope having the image analysis device according to claim 10, wherein the classification value is one of a maximum value, a minimum value, an average value, a relative difference, and a relative ratio of the pixel data of the analysis area.

12. The scanning type optical microscope having the image analysis device according to claim 10, wherein the pixel data are fluorescence intensities obtained from a two-dimensional or three-dimensional observation area.

13. The scanning type optical microscope having the image analysis device according to claim 10, wherein the calculation means calculates a minimum value of the pixel data of every group, adds the calculated minimum value to the pixel data of all the new images, and calculates the correlation value for the new images to which the minimum value has been added.

14. The scanning type optical microscope having the image analysis device according to claim 10, wherein the calculation means calculates the number of the images included in each group, and calculates the average image on the basis of the number of the images of every group.

15. The scanning type optical microscope having the image analysis device according to claim 10, wherein the calculation means reconstitutes each of the images on the basis of the pixel data of the new images, and calculates the correlation value for the reconstituted images.

16. The scanning type optical microscope having the image analysis device according to claim 10, wherein the images are obtained by a scanning type microscope.

17. The scanning type optical microscope having the image analysis device according to claim 10, wherein the calculation means estimates the number of molecules or a diffusion constant of a two-dimensional or three-dimensional observation area in accordance with the following Equation (1) and the following Equation (2):

$$G_{sa}(\xi, \psi) = \frac{\Sigma I(x, y) * I(x+\xi, y+\psi)/M_{11}}{(\Sigma I(x, y)/M_1)^2} \quad (1)$$

where $G_{sa}$ is a space auto-correlation value of RICS, I is the pixel data, x and y are spatial coordinates of a measurement point, $\xi$ and $\psi$ are change amounts of the spatial coordinates from the measurement point, $M_{11}$ is the number of data product sum calculation times, and $M_1$ is the total number of the data, $$G_{sc}(\xi, \psi) = \frac{\Sigma I_1(x, y) * I_2(x+\xi, y+\psi)/M_{12}}{(\Sigma I_1(x, y)/M_1) * (\Sigma I_2(x, y)/M_2)} \quad (2)$$

where $G_{sc}$ is a space cross-correlation value of the RICS, $I_1$ is the pixel data of channel 1, $I_2$ is the pixel data of channel 2, x and y are the spatial coordinates of the measurement point, $\xi$ and $\psi$ are the change amounts of the spatial coordinates from the measurement point, $M_{12}$ is the number of the data product sum calculation times, $M_1$ is the total number of the data of the channel 1, and $M_2$ is the total number of the data of the channel 2.

18. The scanning type optical microscope having the image analysis device according to claim 17, wherein the calculation means performs fitting of the calculation result of the space correlation value by use of the following Equation (3):

$$G_s(\xi, \psi) = S(\xi, \psi) * G(\xi, \psi) \quad (3)$$

$$S(\xi, \psi) = \exp\left(-\frac{\frac{1}{2} * \left[\left(\frac{2\xi\delta_r}{W_0}\right)^2 + \left(\frac{2\psi\delta_r}{W_0}\right)^2\right]}{\left(1 + \frac{4D(\tau_p\xi + \tau_l\psi)}{W_0^2}\right)}\right)$$

$$G(\xi, \psi) = \frac{\gamma}{N}\left(\left(1 + \frac{4D(\tau_p\xi + \tau_l\psi)}{W_0^2}\right)^{-1} * \left(1 + \frac{4D(\tau_p\xi + \tau_l\psi)}{W_z^2}\right)^{-\frac{1}{2}}\right)$$

where $G_s$ is the space correlation value of the RICS, S is an influence of the scanning in the analysis of the RICS, G is an influence of time delay in the analysis of the RICS, D is a diffusion constant, $\xi$ and $\psi$ are the change amounts of the spatial coordinates from the measurement point, $\delta_r$ is a pixel size, N is the number of the molecules, $W_0$ is a radius of an excitation laser beam in a lateral direction, $W_z$ is a radius of the excitation laser beam in a vertical direction, $\tau_p$ is a pixel time, $\tau_l$ is a line time, and $\gamma$ is an arbitrary constant.

* * * * *